United States Patent
Ishihara

(10) Patent No.: US 7,919,761 B2
(45) Date of Patent: Apr. 5, 2011

(54) FLUORESCENCE OBSERVATION APPARATUS

(75) Inventor: Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/883,932

(22) Filed: Sep. 16, 2010

(65) Prior Publication Data

US 2011/0001061 A1    Jan. 6, 2011

Related U.S. Application Data

(63) Continuation of application No. PCT/JP2009/055051, filed on Mar. 16, 2009.

(30) Foreign Application Priority Data

Mar. 24, 2008    (JP) ................................. 2008-076339

(51) Int. Cl.
G01J 1/58    (2006.01)
(52) U.S. Cl. .................. 250/458.1; 250/459.1
(58) Field of Classification Search ............... 250/458.1, 250/459.1
See application file for complete search history.

(56) References Cited

U.S. PATENT DOCUMENTS 6,070,096 A * 5/2000 Hayashi ........................ 600/477

FOREIGN PATENT DOCUMENTS

| JP | 2003-339622 | 12/2003 |
|---|---|---|
| JP | 2003-339623 | 12/2003 |
| JP | 2004-008230 | 1/2004 |
| JP | 2007-125245 | 5/2007 |

OTHER PUBLICATIONS

International Search Report dated May 26, 2009.

* cited by examiner

*Primary Examiner* — David P Porta
*Assistant Examiner* — Mark R Gaworecki
(74) *Attorney, Agent, or Firm* — Scully, Scott, Murphy & Presser, P.C.

(57) ABSTRACT

Clearly observing the state of an examination site is made by sufficiently suppressing the influence of residues. Fluorescence observation apparatus includes: a light source emits excitation light for irradiating the vicinity of an examination site; a fluorescence information acquisition unit acquires information about fluorescence emitted from the vicinity of the examination site through the irradiation with the excitation light from the light source; a residue fluorescence information acquisition unit acquires information about fluorescence emitted from residues selectively dyed with a fluorescent dye, through the irradiation with the excitation light from the light source; and a fluorescence information correction unit generates fluorescence information about the examination site in which the fluorescence from the residues is suppressed, based on the fluorescence information from the vicinity of the examination site, acquired by the fluorescence information acquisition unit, and the fluorescence information from the residues, acquired by the residue fluorescence information acquisition unit.

5 Claims, 8 Drawing Sheets

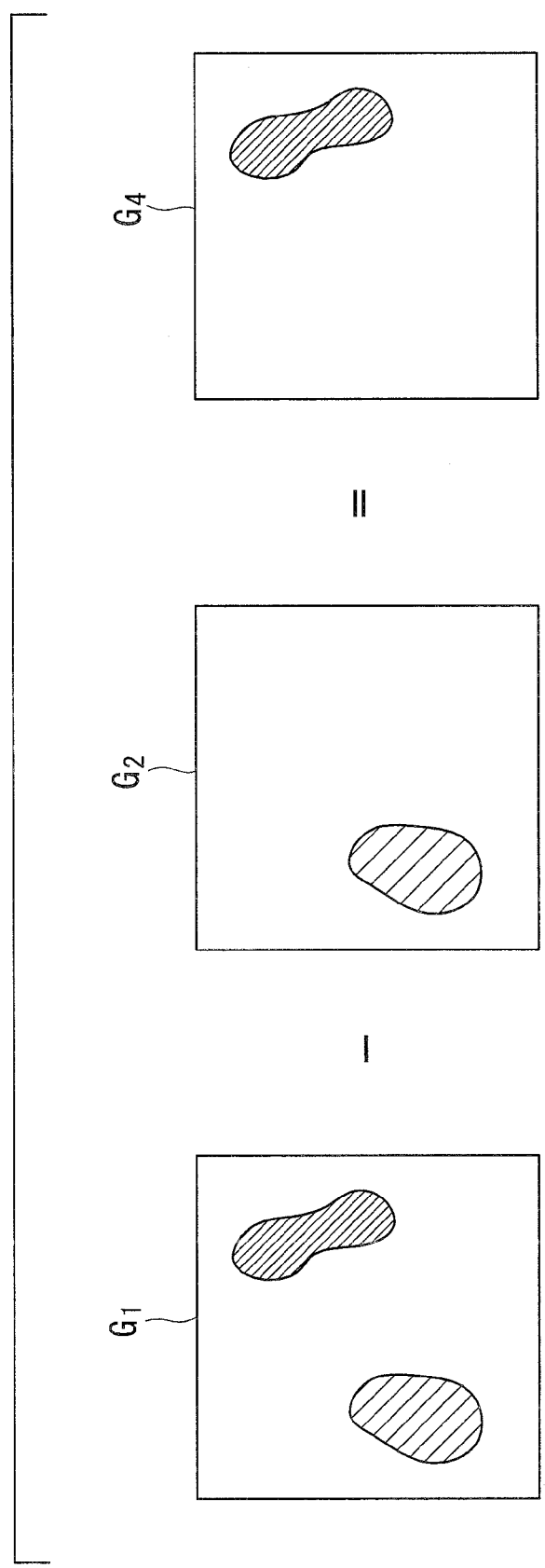

FLUORESCENCE OBSERVATION APPARATUS

CROSS-REFERENCE TO RELATED APPLICATIONS

1. Technical Field

The present invention relates to a fluorescence observation apparatus.

This application is based on Japanese Patent Application No. 2008-076339, the content of which is incorporated herein by reference.

2. Background Art

A conventionally known observation apparatus acquires fluorescence in a wavelength band that is characteristic of residues (such as stool remaining in the large intestine and food being digested in the stomach) and fluorescence in a wavelength band that depends on a lesion in order to remove the influence of such fluorescence emitted from the residues from image information about fluorescence emitted through irradiation with excitation light (for example, see Japanese Unexamined Patent Application, Publication No. 2003-339623).

DISCLOSURE OF INVENTION

However, since the spectra of the residues vary between individuals and greatly depend on the color etc. of food ingested before examination, a wavelength band that is characteristic of the residues cannot be identified simply, and thus, a fluorescence image of the residues cannot be sufficiently removed from a fluorescence image in a wavelength band that depends on a lesion.

An object of the present invention is to provide a fluorescence observation apparatus capable of clearly observing the state of an examination site by sufficiently suppressing the influence of residues.

According to one aspect of the present invention, there is provided a fluorescence observation apparatus including: a light source that emits excitation light for irradiating the vicinity of an examination site; a fluorescence information acquisition unit that acquires information about fluorescence emitted from the vicinity of the examination site through the irradiation with the excitation light from the light source; a residue fluorescence information acquisition unit that acquires information about fluorescence emitted from residues selectively dyed with a fluorescent dye, through the irradiation with the excitation light from the light source; and a fluorescence information correction unit that generates fluorescence information about the examination site in which the fluorescence from the residues is suppressed, based on the fluorescence information from the vicinity of the examination site, acquired by the fluorescence information acquisition unit, and the fluorescence information from the residues, acquired by the residue fluorescence information acquisition unit.

According to the aspect of the present invention, when excitation light emitted from the light source is radiated to the vicinity of the examination site, information about fluorescence emitted from the vicinity of the examination site is acquired by the fluorescence information acquisition unit, and information about fluorescence emitted from residues selectively dyed with a fluorescent dye is acquired by the residue fluorescence information acquisition unit. Then, the fluorescence information correction unit generates fluorescence information about the examination site, in which the fluorescence from the residues is suppressed, based on the fluorescence information from the vicinity of the examination site, acquired by the fluorescence information acquisition unit, and the fluorescence information from the residues, acquired by the residue fluorescence information acquisition unit. Thus, it is possible to acquire fluorescence information in a wavelength band that depends on a lesion, in which the fluorescence information of the residues is suppressed, to clearly observe the state of the examination site. The fluorescent dye for selectively dying residues is ICG (indocyanine green), for example.

In the above-described aspect, the fluorescence information may be a fluorescence image.

In the above-described aspect of the invention, it is preferred that the fluorescence information correction unit subtract the fluorescence information from the residues, acquired by the residue fluorescence information acquisition unit, from the fluorescence information from the vicinity of the examination site, acquired by the fluorescence information acquisition unit.

With this operation, the state of the examination site can be clearly observed by removing the influence of the fluorescence information about the residues.

In the above-described aspect of the invention, the fluorescence information correction unit may divide the fluorescence information from the vicinity of the examination site, acquired by the fluorescence information acquisition unit, by the fluorescence information from the residues, acquired by the residue fluorescence information acquisition unit.

With this operation, the state of the examination site can be clearly observed by reducing the influence of the fluorescence information about the residues.

In the above-described aspect of the invention, the fluorescence information correction unit may compare fluorescence intensity in the fluorescence information from the residues, acquired by the residue fluorescence information acquisition unit, with a predetermined threshold to judge whether a residue remains, and reduce the fluorescence intensity at an area where it has been judged that the residue remains, in the fluorescence information from the vicinity of the examination site, acquired by the fluorescence information acquisition unit.

With this operation, the state of the examination site can be clearly observed by acquiring fluorescence information about the examination site in which the influence of the residues is removed, without directly using the fluorescence information about the residues.

According to the present invention, an advantage is afforded in that the state of an examination site can be clearly observed by sufficiently suppressing the influence of residues.

BRIEF DESCRIPTION OF DRAWINGS

FIG. 5 is a view for explaining a process of subtracting a second fluorescence image from a first fluorescence image.

BEST MODE FOR CARRYING OUT THE INVENTION

A fluorescence observation apparatus 1 according to one embodiment of the present invention will be described below with reference to FIGS. 1 to 6.

Figure 1:
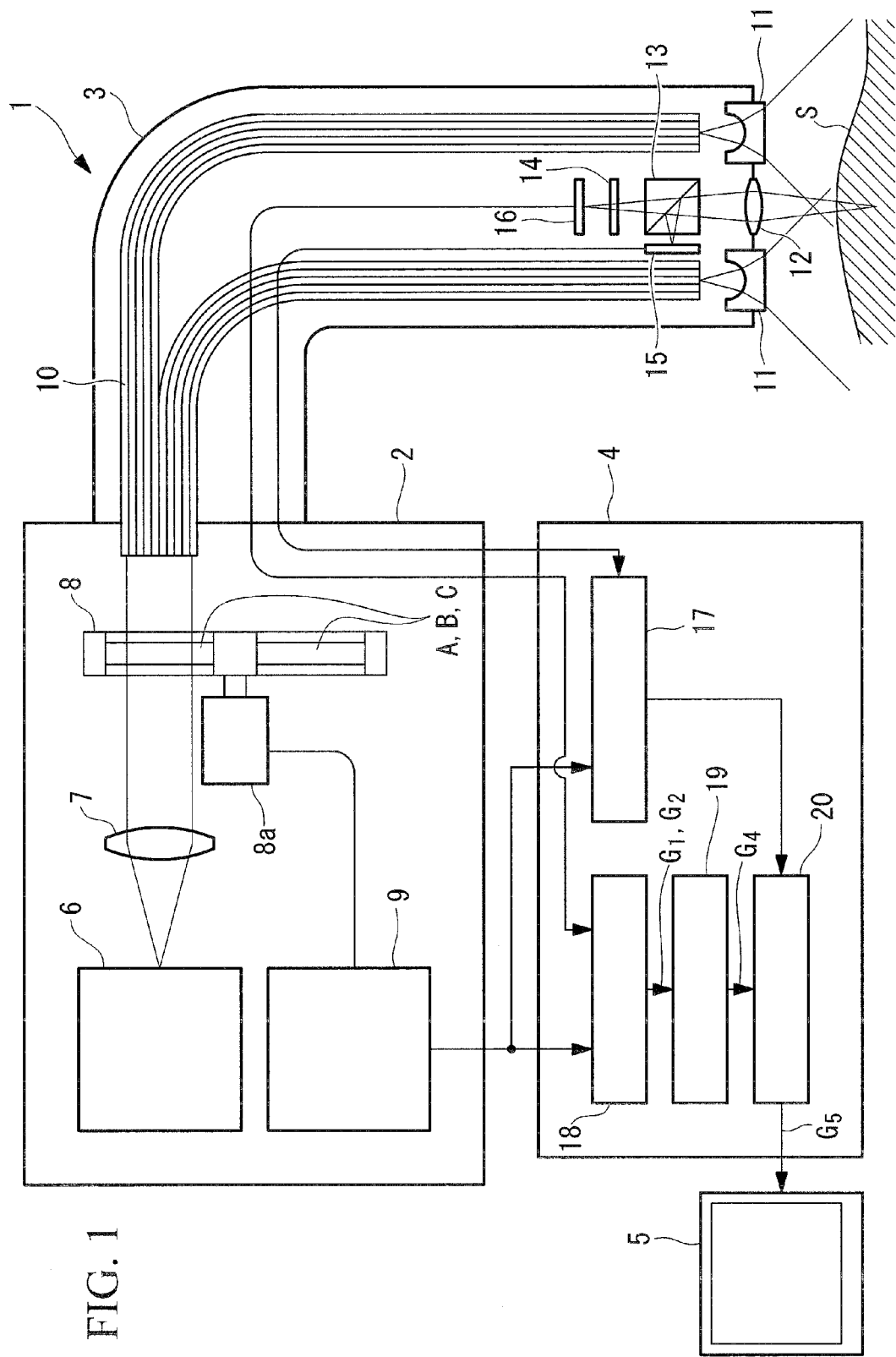
FIG. 1 is a schematic view showing a fluorescence observation apparatus according to one embodiment of the present invention.

As shown in FIG. 1, the fluorescence observation apparatus 1 according to this embodiment includes a light source section 2, an insertion section 3, an image processing section 4, and a monitor 5.

The light source section 2 includes a white light source 6 that emits white light, a collimator lens 7 that converts the white light from the white light source 6 into approximately collimated light, a rotary filter 8 that extracts light in a predetermined wavelength band from the white light, and a filter controller 9 that controls the rotary filter 8.

Figure 2:
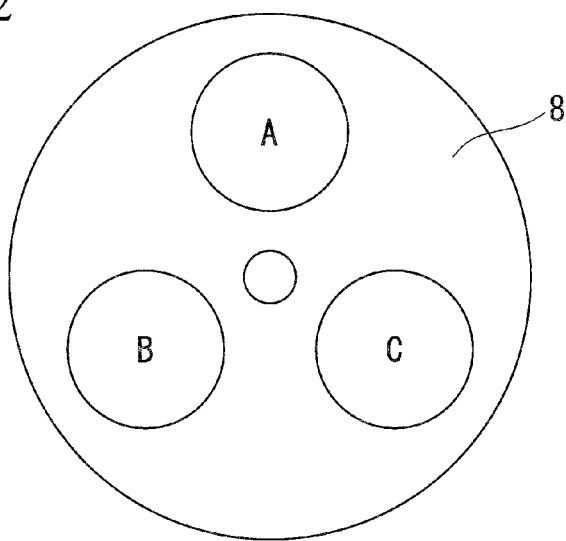
FIG. 2 is a view showing an example rotary filter provided in the fluorescence observation apparatus in FIG. 1.
Figure 3A:
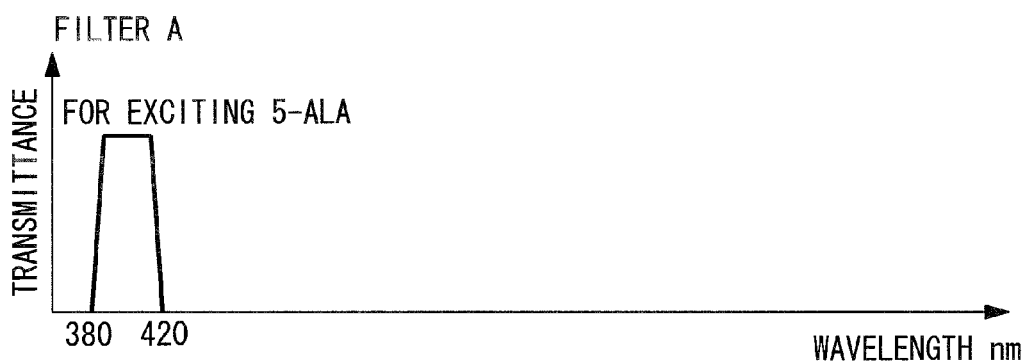
FIG. 3A is a graph showing one example of the transmittance characteristics of individual filters of the rotary filter in FIG. 2 and an excitation light cut filter.
Figure 3B:
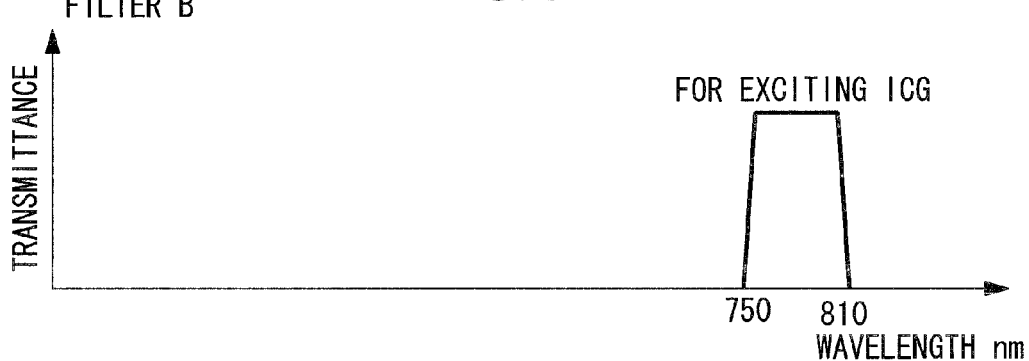
FIG. 3B is a graph showing one example of the transmittance characteristics of the individual filters of the rotary filter in FIG. 2 and the excitation light cut filter.
Figure 3C:
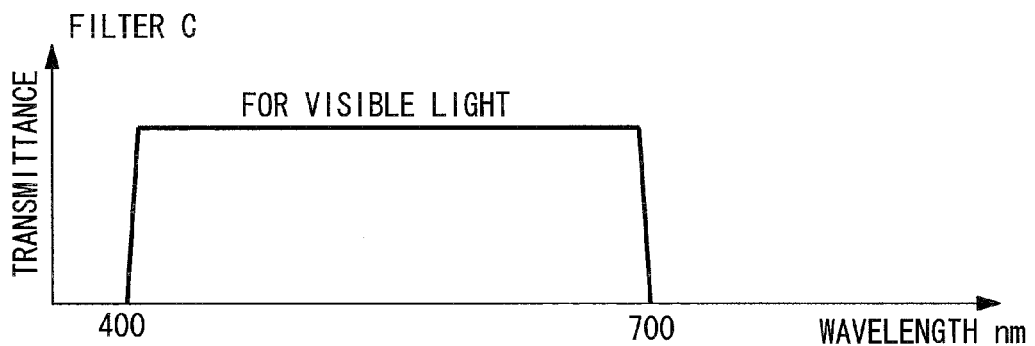
FIG. 3C is a graph showing one example of the transmittance characteristics of the individual filters of the rotary filter in FIG. 2 and the excitation light cut filter.
Figure 3D:
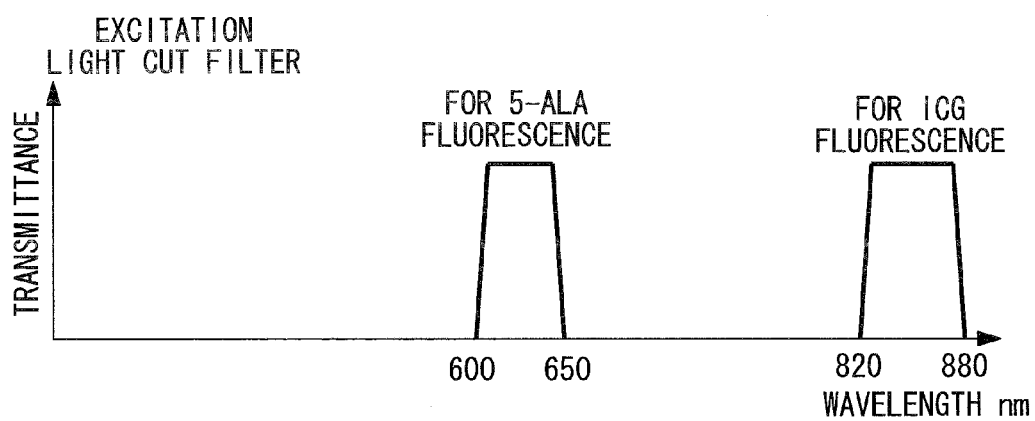
FIG. 3D is a graph showing one example of the transmittance characteristics of the individual filters of the rotary filter in FIG. 2 and the excitation light cut filter.
Figure 4A:
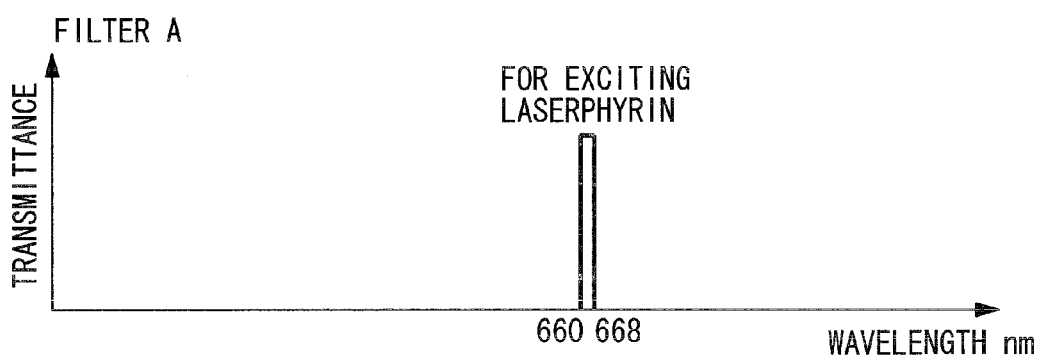
FIG. 4A is a graph showing another example of the transmittance characteristics of the individual filters of the rotary filter in FIG. 2 and the excitation light cut filter.
Figure 4B:
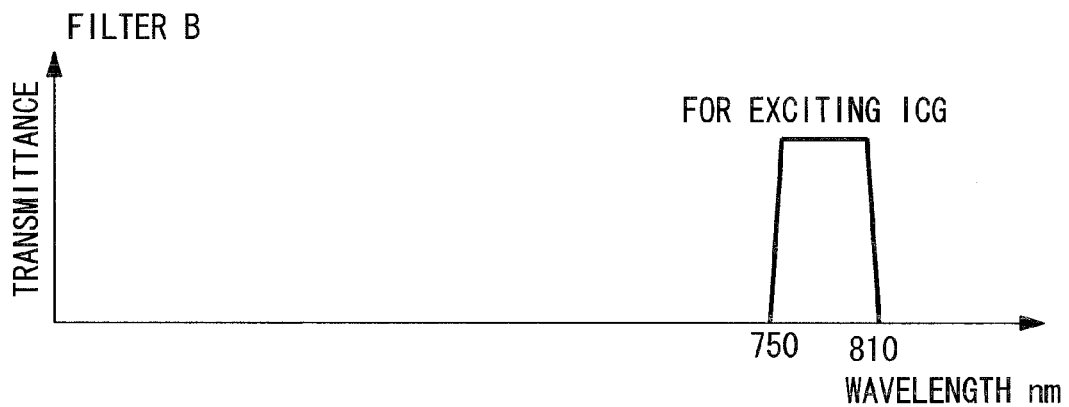
FIG. 4B is a graph showing another example of the transmittance characteristics of the individual filters of the rotary filter in FIG. 2 and the excitation light cut filter.
Figure 4C:
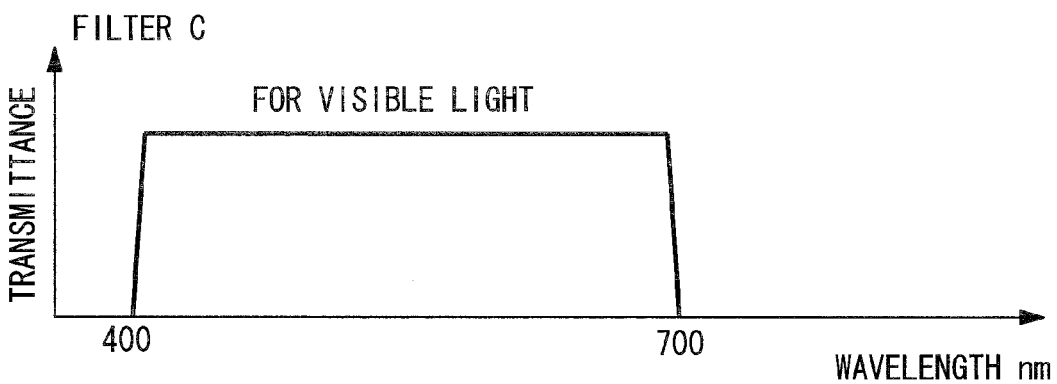
FIG. 4C is a graph showing another example of the transmittance characteristics of the individual filters of the rotary filter in FIG. 2 and the excitation light cut filter.
Figure 4D:
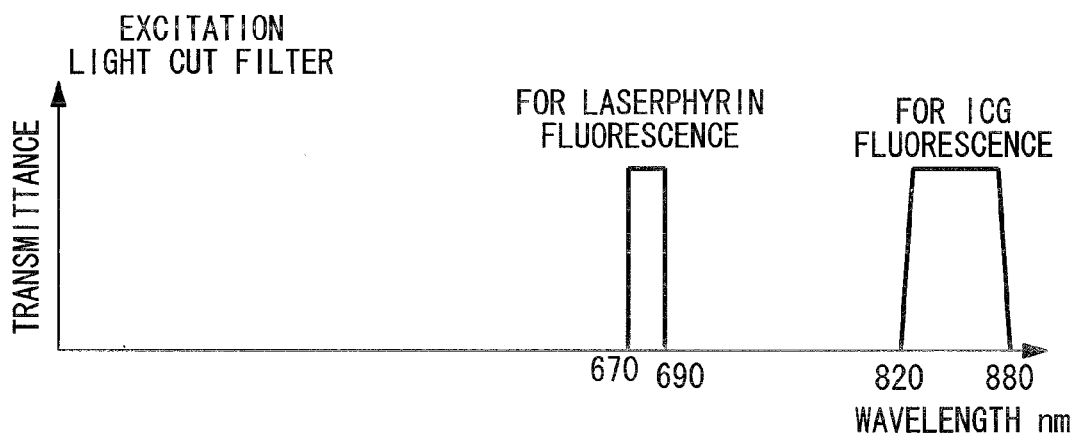
FIG. 4D is a graph showing another example of the transmittance characteristics of the individual filters of the rotary filter in FIG. 2 and the excitation light cut filter.

As shown in FIG. 2, the rotary filter 8 is provided with three different filters A, B, and C. As shown in FIGS. 3A to 3D, the filters A, B, and C have transmittance characteristics such that the filter A transmits light in a wavelength band from 380 nm to 420 nm for exciting 5-ALA (5-aminolevulinic acid), the filter B transmits light in a wavelength band from 750 nm to 810 nm for exciting ICG (indocyanine green), and the filter C transmits light in a wavelength band from 400 nm to 700 nm for visible light.

The light in the wavelength band from 380 nm to 420 nm extracted by the filter A has a characteristic such that, when the light irradiates the vicinity of an examination site S, which is a body tissue, the light is absorbed by blood vessels existing in the body tissue of the examination site S or by blood flowing in the blood vessels. The light in this wavelength band has a characteristic whereby the light excites a fluorescent substance such as 5-ALA existing in blood and makes it emit fluorescence in a wavelength band from 600 nm to 650 nm.

The light in the wavelength band from 750 nm to 810 nm extracted by the filter B has a characteristic whereby the light excites a fluorescent agent such as ICG and makes it emit fluorescence in a wavelength band from 820 nm to 880 nm.

When a motor 8a is rotationally driven in response to a command signal from the filter controller 9, the rotary filter 8 sequentially switches among the filters A, B, and C to irradiate light in the different wavelength bands to the same examination site S.

The filter controller 9 outputs, as a trigger signal, information about the filter A, B, or C disposed in the light path to the image processing section 4, to be described later.

The insertion section 3 is formed long, narrow, and curvable so as to be able to be inserted into a body cavity, for example. The insertion section 3 includes light guide fibers 10 that guide light emitted from the light source section 2, lenses 11 that spread the light guided to the tip by the light guide fibers 10 to irradiate it to the examination site S, an objective lens 12 that collects reflected light or fluorescence returned from the examination site S, a dichroic mirror 13 that separates the collected reflected light and fluorescence into different light paths, an excitation light cut filter 14 that blocks excitation light contained in the separated fluorescence, a reflected-light image acquisition device 15 that detects the separated reflected light, and a fluorescence image acquisition device 16 that detects fluorescence that has passed through the excitation light cut filter 14.

As shown in FIGS. 3A to 3D, the excitation light cut filter 14 has a transmittance characteristic whereby it transmits, of light separated from the reflected light by the dichroic mirror 13, only fluorescence in a wavelength band from 600 nm to 650 nm corresponding to autofluorescence and fluorescence in a wavelength band from 820 nm to 880 nm corresponding to agent fluorescence and blocks light in the other wavelength bands.

The reflected-light image acquisition device 15 and the fluorescence image acquisition device 16 are each formed of a solid-state image acquisition device such as a CCD.

The image processing section 4 includes a reflected-light image generation unit 17 that generates a reflected-light image based on reflected-light image information sent from the reflected-light image acquisition device 15 and a trigger signal sent from the filter controller 9, a fluorescence image generation unit 18 that generates a fluorescence image based on fluorescence image information sent from the fluorescence image acquisition device 16 and trigger signals sent from the filter controller 9, an image calculation unit 19 that carries out image calculation by using fluorescence image information sent from the fluorescence image generation unit 18, and an image generation unit 20 that generates an image to be displayed on the monitor 5 by using the reflected-light image generated in the reflected-light image generation unit 17 and a calculated image generated in the image calculation unit 19.

The reflected-light image generation unit 17 recognizes a time period when the filter A is disposed in the light path based on a trigger signal sent from the filter controller 9 and outputs image information sent from the reflected-light image acquisition device 15 during this time period, as a reflected-light image.

The fluorescence image generation unit 18 recognizes time periods when the filters A and B are disposed in the light path based on trigger signals sent from the filter controller 9 and outputs first fluorescence image $G_1$ information sent from the fluorescence image acquisition device 16 during the time period when the filter A is disposed in the light path and second fluorescence image $G_2$ information sent from the fluorescence image acquisition device 16 during the time period when the filter B is disposed in the light path.

The image calculation unit 19 subtracts a second image $G_2$ from a first image $G_1$, for example.

The image generation unit 20 combines a reflected-light image $G_3$ sent from the reflected-light image generation unit 17 and a calculated image $G_4$ output from the image calculation unit 19 to generate a combined image $G_5$.

A description will be given below of a case in which the examination site S is observed using the thus-configured fluorescence observation apparatus 1 according to this embodiment.

To observe the examination site S using the fluorescence observation apparatus 1 of this embodiment, ICG is administered approximately 17 hours before the start of observation, 5-ALA is administered approximately 4 hours before the start of observation, and an intestinal cleaning agent is ingested before observation to excrete the stool in the intestines.

In this state, the insertion section 3 is inserted into the large intestine to start observation.

The insertion section 3 is inserted into the large intestine, and the tip thereof is disposed to face the examination site S. In this state, the light source section 2 is operated, and light in the wavelength band from 380 nm to 420 nm, light in the wavelength band from 750 nm to 810 nm, and white light in the wavelength band from 400 nm to 700 nm are switched among to irradiate the same examination site S. The white light in the wavelength band from 400 nm to 700 nm is used as visible light to confirm the examination site S, when operating the insertion section 3; however, a description thereof will be omitted.

Through irradiation with the light in the wavelength band 380 nm to 420 nm, the first fluorescence image $G_1$ information is acquired by the fluorescence image acquisition device 16. Through irradiation with the light in the wavelength band 750 nm to 810 nm, the second fluorescence image $G_2$ information is acquired by the fluorescence image acquisition device 16.

Through irradiation with the white light in the wavelength band 400 nm to 700 nm, the reflected-light image $G_3$ information is acquired by the reflected-light image acquisition device 15.

In the fluorescence observation apparatus 1 according to this embodiment, the first fluorescence image $G_1$ information and the second fluorescence image $G_2$ information acquired by the fluorescence image acquisition device 16 are sent to the image calculation unit 19 and are subjected to subtraction processing. Specifically, as shown in FIG. 5, the second fluorescence image $G_2$ information is subtracted from the first fluorescence image $G_1$ information, thereby generating the calculated image $G_4$.

The ICG administered before the observation flows in the blood vessels throughout the body, is eventually trapped in the liver, and, mixed with bile, flows from the gallbladder toward the duodenum. In general, such a phenomenon starts to be observed when approximately 15 minutes have elapsed after the administration of the ICG, and a similar phenomenon occurs for 24 hours after the administration, until the all ICG has been excreted after passing through the liver, the gallbladder, and the duodenum.

During this process, the ICG is not structurally destroyed, absorbed via the intestines, or excreted from enterohepatic circulation or the kidneys. Therefore, in the process where food ingested by the subject is digested in the stomach, the duodenum, the small intestine, and the large intestine, the ICG contained in bile is absorbed to form stool. Furthermore, when approximately 15 minutes have elapsed after the administration of the ICG, the ICG hardly exists in blood or tissues except the liver, the gallbladder, and the surfaces of hollow organs, such as the duodenum, the small intestine, and the large intestine.

As described above, for example, when ICG is administered approximately 17 hours before the start of observation, 5-ALA is administered approximately 4 hours before the start of observation, and an intestinal cleaning agent is ingested before observation to rinse out the stool in the intestines and the ICG remaining on the surfaces of the hollow organs, it is possible to produce a situation where the examination site S that contains 5-ALA and the remaining stool (residue) that contains the ICG around the examination site S exist.

Therefore, the second fluorescence image $G_2$ information obtained through the irradiation with light in the wavelength band from 750 nm to 810 nm for exciting ICG is fluorescence image information obtained when the residue is made to be specifically luminous.

On the other hand, since light in the wavelength band from 380 nm to 420 nm causes all areas containing fluorescent substances excited by this light to emit fluorescence, the examination site S and residues located in the vicinity thereof are also made to be luminous.

Therefore, with only the first fluorescence image $G_1$ information, since fluorescence emitted from the examination site S and fluorescence emitted from the residues located in the vicinity thereof are mixed, the examination site S cannot be clearly observed; however, according to the fluorescence observation apparatus 1 of this embodiment, since the second fluorescence image $G_2$ information that contains only the fluorescence emitted from the residues is removed from the first fluorescence image $G_1$ information, the examination site S can be clearly observed.

Figure 6:
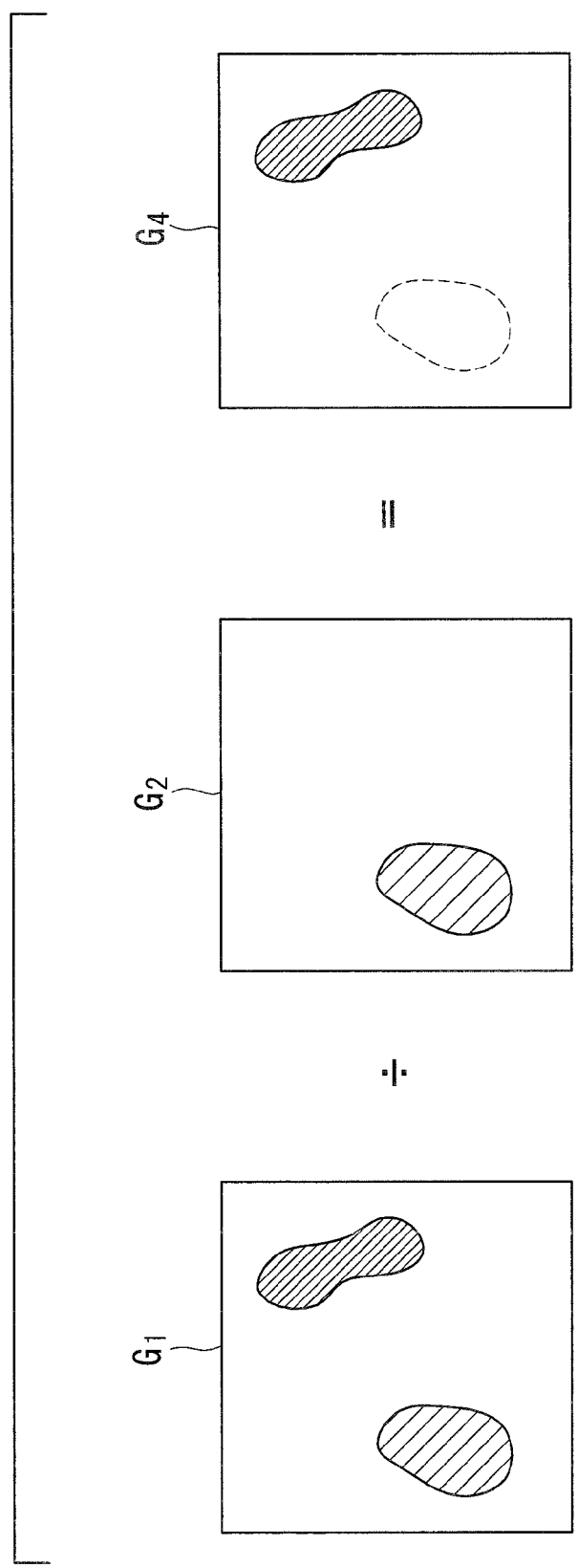
FIG. 6 is a view for explaining a process of dividing the first fluorescence image by the second fluorescence image.

Note that, in this embodiment, the image calculation unit 19 subtracts the second fluorescence image $G_2$ information from the first fluorescence image $G_1$ information to remove the influence of residues in the fluorescence image; however, instead of the subtraction, as shown in FIG. 6, the first fluorescence image $G_1$ information may be divided by the second fluorescence image $G_2$ information. With this operation, the influence of residues in the fluorescence image can also be sufficiently suppressed.

Although 5-ALA is used as an example of the fluorescent agent administered into the examination site S, the fluorescent agent is not limited thereto, and, for example, Laserphyrin may be administered, as shown in FIGS. 4A to 4D.

In this embodiment, although the second fluorescence image $G_2$ information is subtracted from the first fluorescence image $G_1$ information, an operation may be performed in which the fluorescence intensity at each pixel in the second fluorescence image $G_2$ information is compared with a predetermined threshold, and, for an area where the fluorescence intensity is larger than the predetermined threshold, the fluorescence intensity of the corresponding area in the first fluorescence image $G_1$ is reduced. With this operation, it is possible to correct the first fluorescence image $G_1$ such that the influence of residues is removed only from an area that is strongly influenced by the residues.

Figure 7:
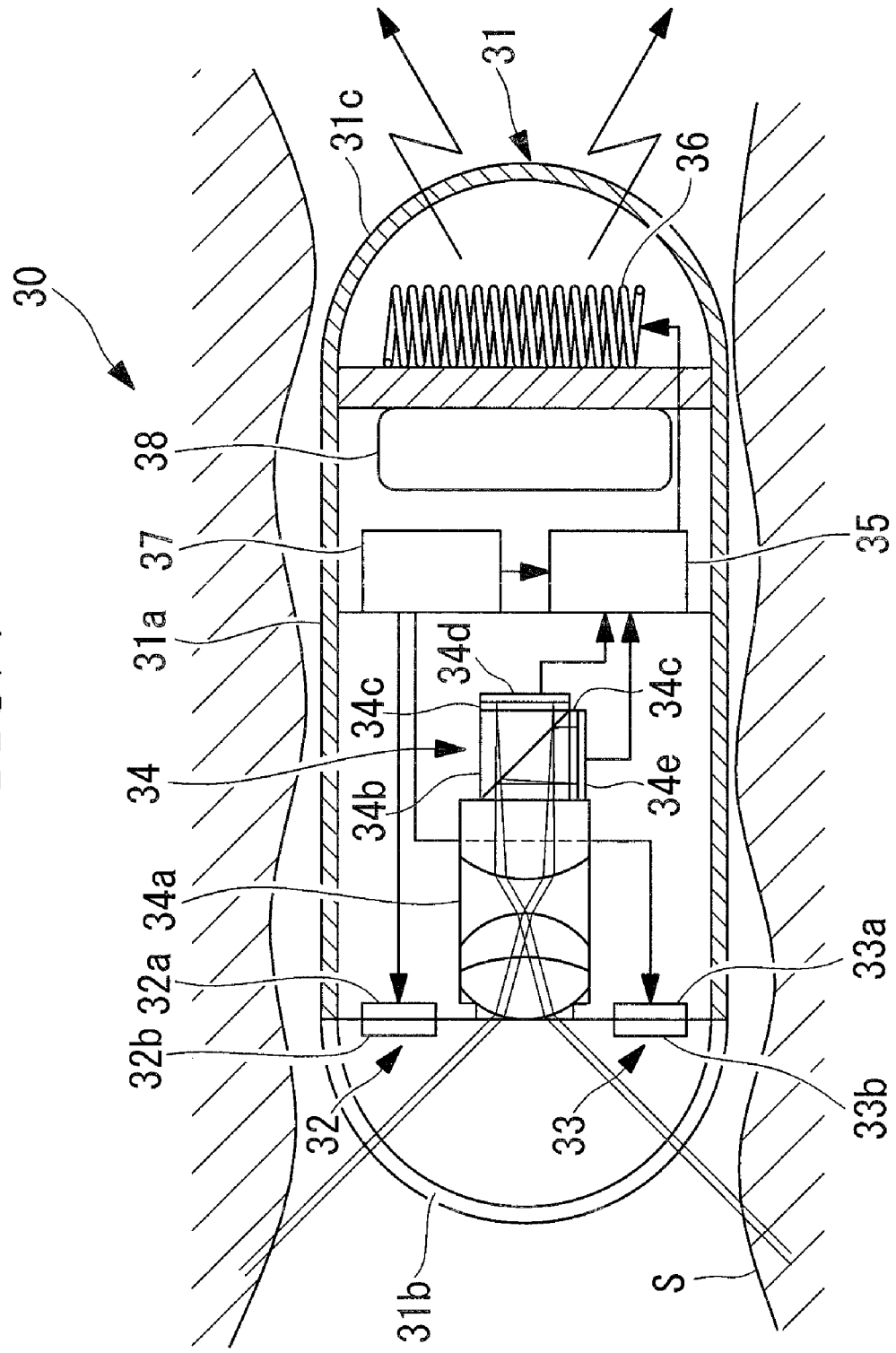
FIG. 7 is a schematic view showing a modification of the fluorescence observation apparatus in FIG. 1.

In this embodiment, the endoscopic-type fluorescence observation apparatus 1, in which the flexible, long, and narrow insertion section 3 is inserted in the large intestine, is used as an example; however, instead of this, a capsule-type fluorescence observation apparatus 30 may be employed, as shown in FIG. 7.

The fluorescence observation apparatus 30 includes a capsule-shaped housing 31 that encapsulates both ends of a cylindrical housing main body 31a by using a hemispherical transparent window 31b and a hemispherical end plate 31c, first and second excitation light sources 32 and 33 that are accommodated in the housing 31 and that irradiate excitation light through the transparent window 31b, an information acquisition unit 34 that takes an image of the examination site S, a luminance information correction unit 35 that generates luminance information in which the influence of residues is suppressed, based on the luminance information acquired by the information acquisition unit 34, an antenna (transmission unit) 36 that wirelessly transmits the generated luminance information to the outside of the housing 31, a control unit (determination unit) 37 that controls those units, and a battery 38 that supplies power to each of those units.

The excitation light sources 32 and 33 include, for example, LEDs 32a and 33a that emit broadband light and excitation light filters 32b and 33b that transmit, of the light emitted from the LEDs 32a and 33a, only light in an excitation wavelength to emit it through the transparent window 31b. Examples of the excitation light filter 32b include a Laserphyrin exciting filter A, and examples of the excitation light filter 33b include an ICG exciting filter B.

The information acquisition unit 34 includes an optical system 34a that collects fluorescence entering the housing 31 through the transparent window 31b, a dichroic mirror 34b that separates excitation light in respective wavelengths from the collected fluorescence, an excitation light cut filter 34c that blocks excitation light that has been transmitted through or reflected at the dichroic mirror 34b, and photodetectors 34d and 34e that detect the intensity of fluorescence from which the excitation light has been removed.

The control unit 37 controls the lighting timing of the excitation light source 32 and the excitation light source 33, stores, in a luminance information correction unit 35, the fluorescence intensity detected by the photodetector 34d during a time period when excitation light is emitted from the excitation light source 32 provided with the filter 32b, as first fluorescence intensity information, and stores, luminance information correction unit 35, the fluorescence intensity detected by the photodetector 34e during a time period when excitation light is emitted from the excitation light source 33 provided with the filter 33b, as second fluorescence intensity information.

Figure 8:
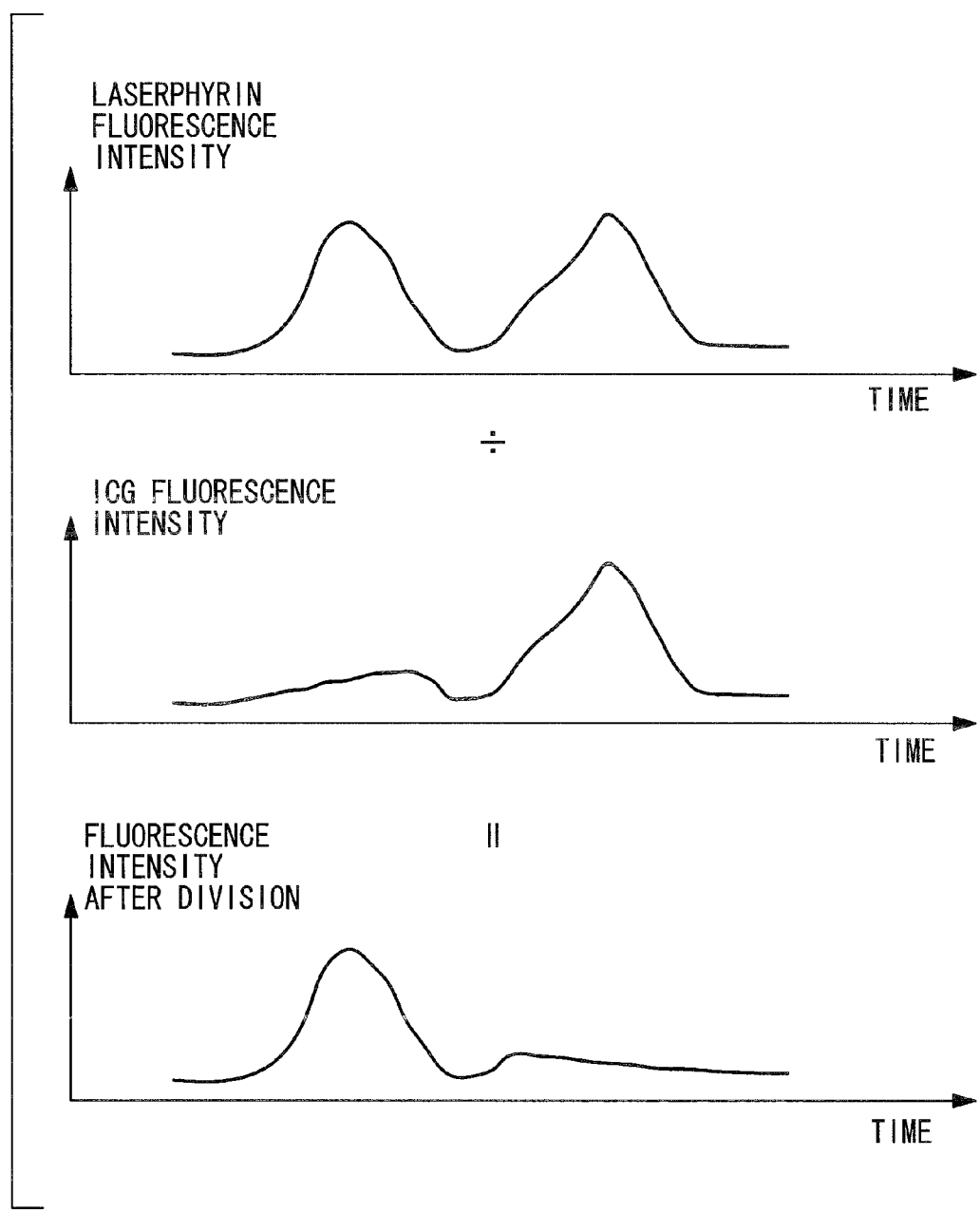
FIG. 8 is a view for explaining a process of dividing first fluorescence information obtained by a fluorescence observation apparatus in FIG. 7 by second fluorescence information.

As shown in FIG. 8, the luminance information correction unit 35 divides the first fluorescence luminance information (Laserphyrin fluorescence intensity) by the second fluorescence luminance information (ICG fluorescence intensity). Accordingly, fluorescence luminance information in which the influence of residues is reduced can be obtained.

The invention claimed is:

1. A fluorescence observation apparatus comprising:
   a light source that emits excitation light for irradiating the vicinity of an examination site;
   a fluorescence information acquisition unit that acquires information about fluorescence emitted from the vicinity of the examination site through the irradiation with the excitation light from the light source;
   a residue fluorescence information acquisition unit that acquires information about fluorescence emitted from residues selectively dyed with a fluorescent dye, through the irradiation with the excitation light from the light source; and
   a fluorescence information correction unit that generates fluorescence information about the examination site in which the fluorescence from the residues is suppressed, based on the fluorescence information from the vicinity of the examination site, acquired by the fluorescence information acquisition unit, and the fluorescence information from the residues, acquired by the residue fluorescence information acquisition unit.

2. A fluorescence observation apparatus according to claim 1, wherein the fluorescence information is a fluorescence image.

3. A fluorescence observation apparatus according to claim 1, wherein the fluorescence information correction unit subtracts the fluorescence information from the residues, acquired by the residue fluorescence information acquisition unit, from the fluorescence information from the vicinity of the examination site, acquired by the fluorescence information acquisition unit.

4. A fluorescence observation apparatus according to claim 1, wherein the fluorescence information correction unit divides the fluorescence information from the vicinity of the examination site, acquired by the fluorescence information acquisition unit, by the fluorescence information from the residues, acquired by the residue fluorescence information acquisition unit.

5. A fluorescence observation apparatus according to claim 1, wherein the fluorescence information correction unit compares fluorescence intensity in the fluorescence information from the residues, acquired by the residue fluorescence information acquisition unit, with a predetermined threshold to judge whether a residue remains, and reduces the fluorescence intensity at an area where it has been judged that the residue remains, in the fluorescence information from the vicinity of the examination site, acquired by the fluorescence information acquisition unit.

* * * * *